(12) United States Patent
Fuller et al.

(10) Patent No.: US 7,467,014 B2
(45) Date of Patent: Dec. 16, 2008

(54) COMPACT AND CONFORMAL TELEMETRY ANTENNAS FOR IMPLANTABLE MEDICAL DEVICES

(75) Inventors: Christopher C. Fuller, Minneapolis, MN (US); William D. Verhoef, Andover, MN (US); Gregory J. Haubrich, Champlin, MN (US); Javaid Masoud, Shoreview, MN (US); George C. Rosar, Minneapolis, MN (US); Garry L. Dublin, Maple Grove, MN (US); Piotr Przybyszewski, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 288 days.

(21) Appl. No.: 11/116,983

(22) Filed: Apr. 28, 2005

(65) Prior Publication Data

US 2006/0247712 A1 Nov. 2, 2006

(51) Int. Cl.
*A61N 1/00* (2006.01)
(52) U.S. Cl. .......................... 607/60; 607/36
(58) Field of Classification Search ................. 607/32, 607/31, 59, 60, 36, 37, 38; 343/873, 728, 343/788, 787, 853, 878, 879, 102
See application file for complete search history.

(56) References Cited

U.S. PATENT DOCUMENTS

| | | | | |
|---|---|---|---|---|
| 4,441,498 A | * | 4/1984 | Nordling | 607/32 |
| 5,720,770 A | * | 2/1998 | Nappholz et al. | 607/30 |
| 5,861,019 A | * | 1/1999 | Sun et al. | 607/60 |
| 6,167,312 A | * | 12/2000 | Goedeke | 607/60 |
| 6,240,317 B1 | * | 5/2001 | Villaseca et al. | 607/60 |
| 6,456,256 B1 | * | 9/2002 | Amundson et al. | 343/873 |
| 6,488,704 B1 | * | 12/2002 | Connelly et al. | 623/1.15 |
| 6,505,072 B1 | * | 1/2003 | Linder et al. | 607/32 |
| 6,614,406 B2 | * | 9/2003 | Amundson et al. | 343/873 |
| 6,675,045 B2 | * | 1/2004 | Mass et al. | 607/32 |
| 6,708,065 B2 | * | 3/2004 | Von Arx et al. | 607/60 |
| 7,047,076 B1 | * | 5/2006 | Li et al. | 607/36 |
| 7,149,578 B2 | * | 12/2006 | Edvardsson | 607/17 |
| 2002/0065539 A1 | * | 5/2002 | Von Arx et al. | 607/60 |
| 2002/0123776 A1 | * | 9/2002 | Von Arx et al. | 607/60 |
| 2003/0025645 A1 | | 2/2003 | Amundson et al. | 343/873 |
| 2003/0216793 A1 | | 11/2003 | Karlsson et al. | 607/60 |
| 2004/0088012 A1 | * | 5/2004 | Kroll et al. | 607/9 |
| 2004/0127960 A1 | | 7/2004 | Mass et al. | 607/60 |
| 2004/0215280 A1 | * | 10/2004 | Dublin et al. | 607/36 |
| 2005/0134520 A1 | * | 6/2005 | Rawat et al. | 343/873 |
| 2006/0241724 A1 | * | 10/2006 | Dublin et al. | 607/60 |

* cited by examiner

*Primary Examiner*—Carl H. Layno
*Assistant Examiner*—Jon-Eric C. Morales
(74) *Attorney, Agent, or Firm*—Ingrassia Fisher & Lorenz, P.C.

(57) ABSTRACT

An implantable medical device ("IMD") configured in accordance with an example embodiment of the invention generally includes a housing, a connector header block coupled to the housing, a dielectric sheath located around at least a portion of the housing and/or around at least a portion of the header block, and a telemetry antenna located within the dielectric sheath. The antenna is configured to support far field telemetry with an external device such as a programmer. In one example embodiment, the antenna is configured as a balanced antenna having two separate antenna elements driven 180 degrees out of phase. Each of the antenna elements has a feed point on a perimeter edge of the IMD housing and a floating endpoint. A number of alternate embodiments are also provided.

16 Claims, 11 Drawing Sheets

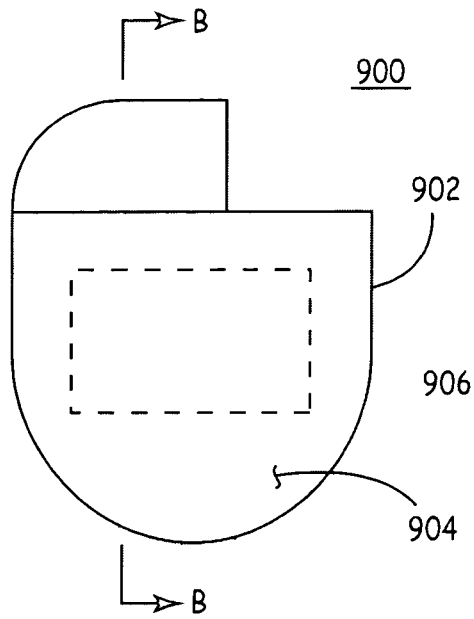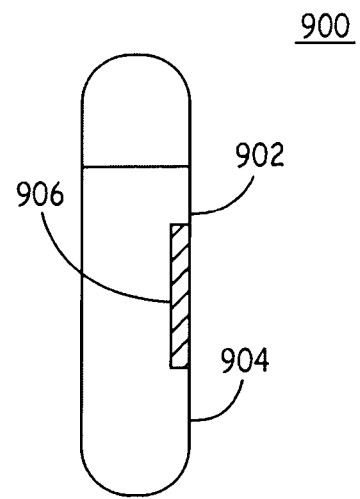
FIG. 25    FIG. 26
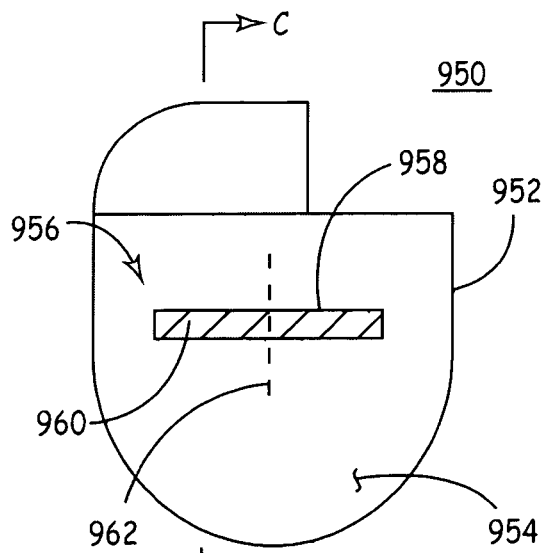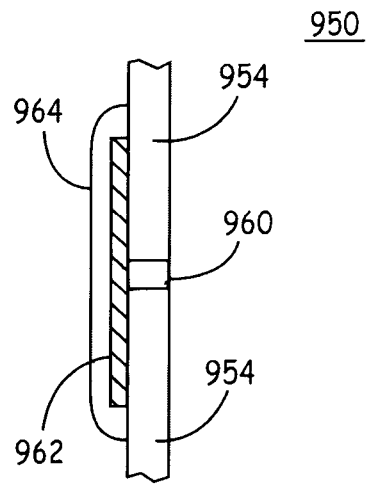
FIG. 27    FIG. 28

COMPACT AND CONFORMAL TELEMETRY ANTENNAS FOR IMPLANTABLE MEDICAL DEVICES

TECHNICAL FIELD

The present invention relates generally to implantable medical devices ("IMDs"). More particularly, the present invention relates to telemetry antennas suitable for deployment in IMDs.

BACKGROUND

IMDs that provide diagnostic and/or therapeutic capabilities are well known in the art. Such IMDs include, without limitation: cardiac pacemakers; implantable cardioverters/defibrillators ("ICDs"); and various tissue, organ, and nerve stimulators or sensors. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads.

The header block is typically molded from a relatively hard, dielectric, non-conductive polymer having a thickness approximating the thickness of the housing. The header block includes a mounting surface that conforms to, and is mechanically affixed against, a mating sidewall surface of the housing.

It has become common to provide a communication link between the hermetically sealed electronic circuitry of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. As the technology has advanced, IMDs have become more complex in possible programmable operating modes, menus of available operating parameters, and capabilities of monitoring, which in turn increase the variety of possible physiologic conditions and electrical signals handled by the IMD. Consequently, such increasing complexity places increasing demands on the programming system.

Conventionally, the communication link between the IMD and the EMD is realized by encoded radio frequency ("RF") transmissions between an IMD telemetry antenna and transceiver and an EMD telemetry antenna and transceiver. The telemetry transmission system that evolved into current common use relies upon the generation of low amplitude magnetic fields by current oscillating in an LC circuit of an RF telemetry antenna in a transmitting mode and the sensing of currents induced by a closely spaced RF telemetry antenna in a receiving mode. Short duration bursts of the carrier frequency are transmitted in a variety of telemetry transmission formats. In some products, the RF carrier frequency is set at 175 kHz, and the prior art contains various RF telemetry antenna designs suitable for use in such applications. To support such products, the EMD is typically a programmer having a manually positioned programming head having an external RF telemetry antenna. Generally, the IMD antenna is disposed within the hermetically sealed housing, however, the typically conductive housing adversely attenuates the radiated RF field and limits the data transfer distance between the programmer head and the IMD RF telemetry antennas to a few inches.

The above-described telemetry system employing the 175 kHz carrier frequency limits the upper data transfer rate, depending upon bandwidth and the prevailing signal-to-noise ratio. Using prior art RF telemetry antennas may result in: (1) a very low radiation efficiency due to feed impedance mismatching and ohmic losses; (2) a radiation intensity that is attenuated in an undesirable manner; and/or (3) poor noise immunity due to the distance between, and poor coupling of, the receiver and transmitter RF telemetry antenna fields.

It has been recognized that "far field" telemetry, or telemetry over distances of a few to many meters from an IMD, would be desirable. Various attempts have been made to provide antennas with an IMD to facilitate far field telemetry. Many proposals have been advanced for eliminating conventional RF telemetry antenna designs and substituting alternative telemetry transmission systems and schemes employing far higher carrier frequencies and more complex signal coding to enhance the reliability and safety of the telemetry transmissions while increasing the data rate and allowing telemetry transmission to take place over a matter of meters rather than inches. A number of alternative IMD telemetry antennas have been proposed. These approaches may be undesirable in that, depending upon the option selected, they may require substantial modification of the housing and/or header block, require additional components added to the housing, reduce the effectiveness of other components (e.g., reducing the available surface area of the can for use as a ground plane or electrode), create a directional requirement (e.g., require that the IMD be oriented in a particular direction during implant for telemetry effectiveness), or add extraneous exposed components that are subject to harmful interaction in the biological environment or require additional considerations during implant (e.g., stub antennas extending outward from the device).

It remains desirable to provide a far field telemetry antenna for an IMD that eliminates drawbacks associated with the IMD telemetry antennas of the prior art. Furthermore, other desirable features and characteristics of the present invention will become apparent from the subsequent detailed description and the appended claims, taken in conjunction with the accompanying drawings and the foregoing technical field and background.

BRIEF SUMMARY

An IMD configured in accordance with an embodiment of the invention includes a far field telemetry antenna that is encapsulated within a dielectric sheath around the outer edge of the IMD can. The antenna topology includes two radiating elements forming a balanced antenna structure. In a practical embodiment of the invention, the antenna is conformal such that it has a minimal impact on the overall IMD volume. The antenna may be optimized to suit the needs of the particular IMD application, e.g., in consideration of the operating environment, the age, sex, or condition of the patient, or implant orientation within the patient.

The above and other aspects of the invention may be carried out in one form by an IMD antenna assembly comprising a dielectric sheath having a first section configured for positioning around at least a portion of the IMD housing perimeter, and a second section configured for positioning around at least a portion of the IMD header block perimeter. The antenna assembly also includes a first antenna element having a first feed point and a first endpoint, where the first endpoint is located in the first section of the dielectric sheath, and a second antenna element having a second feed point and a second endpoint, where the second endpoint is located in the second section of the dielectric sheath.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

FIG. 25 is a front view of an IMD configured in accordance with an alternate embodiment of the invention;

FIG. 26 is a cross sectional view of the IMD shown in FIG. 25, as viewed from line B-B in FIG. 25;

FIG. 27 is a front view of an IMD configured in accordance with an alternate embodiment of the invention; and FIG. 28 is a cross sectional detail view of the IMD shown in FIG. 27, as viewed from line C-C in FIG. 27.

DETAILED DESCRIPTION

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The following description may refer to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

The invention relates to an improved RF telemetry antenna for an IMD. The following description addresses various embodiments in the context of an ICD. However, the invention is intended to be implemented in connection with a wide variety of IMDs. For the sake of brevity, conventional techniques related to RF antenna design, IMD telemetry, RF data transmission, signaling, IMD operation, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna has two primary functions: to convert the electromagnetic power of a downlink telemetry transmission of an EMD telemetry antenna propagated through the atmosphere (and then through body tissues) into a UHF signal that can be processed by the IMD transceiver into commands and data that are intelligible to the IMD electronic operating system; and to convert the uplink telemetry UHF signals of the IMD transceiver electronics into electromagnetic power propagated through the body tissue and the atmosphere so that the EMD can receive the signals.

Figure 1:
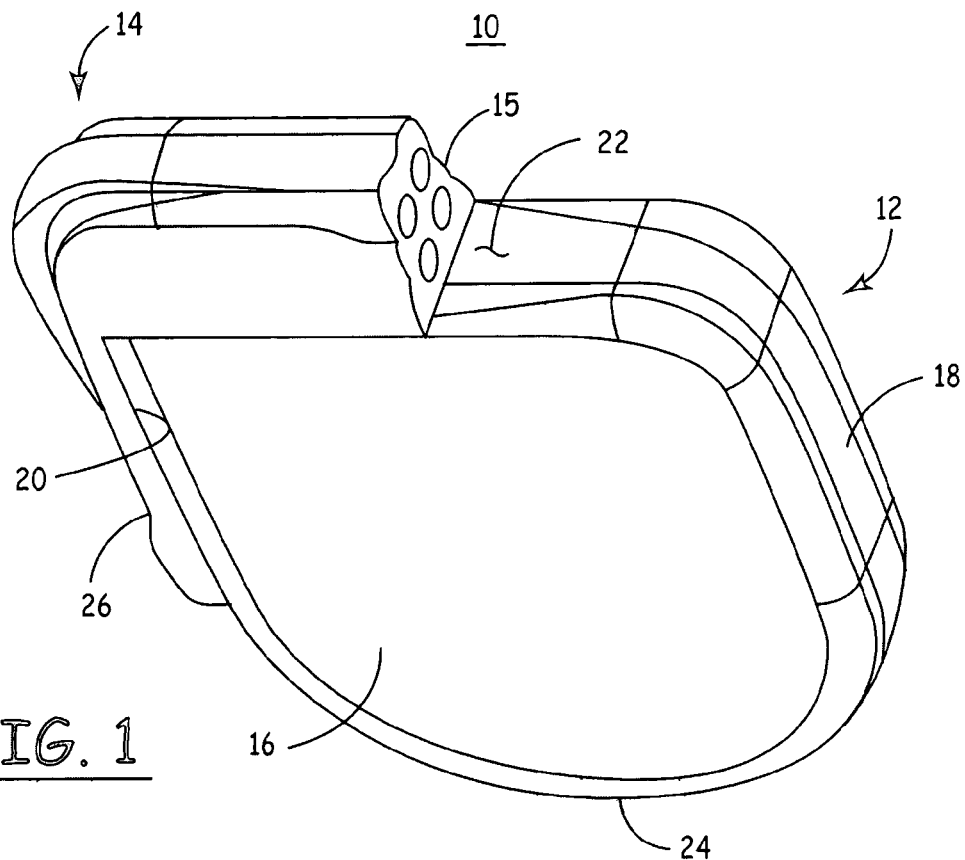
FIG. 1 is a perspective view of an IMD.

FIG. 1 is a perspective view of an IMD 10 having a hermetically sealed housing 12 and a connector header or block 14. A set of IMD leads having electrodes (such as cardioversion/defibrillation electrodes and pace/sense electrodes) disposed in operative relation to a patient's heart are adapted to be coupled to the header block 14 in a manner well known in the art. For example, such leads may enter at an end 15 of header block 14 and be physically and electrically connected to conductive receptacles or other conductive features located within header block 14. IMD 10 is adapted to be implanted subcutaneously in the body of a patient such that it becomes encased within body tissue and fluids, which may include epidermal layers, subcutaneous fat layers, and/or muscle layers.

Hermetically sealed housing 12 is generally circular, elliptical, prismatic, or rectilinear, with substantially planar major sides (only one major side 16 is shown in FIG. 1) joined by perimeter sidewalls. The perimeter sidewalls include a substantially straight first sidewall 18, a substantially straight second sidewall 20 opposing first sidewall 18, a substantially straight upper sidewall 22, and a curvilinear lower sidewall 24 opposing upper sidewall 22. Housing 12 is typically formed from pieces of a thin-walled biocompatible metal such as titanium. Alternatively, as further described below, housing 12 may be formed from one or more pieces of dielectric material such as ceramic. Two half sections of housing 12 may be laser seam welded together using conventional techniques to form a seam extending around the perimeter sidewalls.

Housing 12 and header block 14 are often manufactured as two separate assemblies that are subsequently physically and electrically coupled together. Housing 12 may contain a number of functional elements, components, and features, including (without limitation): a battery; a high voltage output capacitor; integrated circuit ("IC") devices; a processor; memory elements; a therapy module or circuitry; an RF module or circuitry; and an antenna matching circuit. These components may be assembled in spacers and disposed within the interior cavity of housing 12 prior to seam welding of the housing halves. During the manufacturing process, electrical connections are established between components located within housing 12 and elements located within header block 14. For example, housing 12 and header block 14 may be suitably configured with IC connector pads, terminals, feedthrough pins, and other features for establishing electrical connections between the internal therapy module and the therapy lead connectors within header block 14 and for establishing connections between the internal RF module and a telemetry antenna located within header block 14. Structures and techniques for establishing such electrical (and physical) connections are known to those skilled in the art and, therefore, will not be described in detail herein.

Header block 14 is preferably formed from a suitable dielectric material, such as a biocompatible synthetic polymer, tecothane, glass, or ceramic. In some embodiments, the dielectric material of header block 14 passes RF energy that is radiated or received by a telemetry antenna (not shown in FIG. 1) encapsulated within header block 14. The encapsulation of the antenna within header block 14 insulates the antenna from the tissue and fluids after implantation. In practical embodiments, header block 14 is formed from a material having a dielectric constant of approximately 3.0 to 5.0. The specific material for header block 14 may be chosen in response to the intended application of IMD 10, the electrical characteristics of the environment surrounding the implant location, the desired operating frequency range, the desired RF antenna range, and other practical considerations.

In accordance with one example embodiment, header block 14 is approximately one inch wide (measured along upper sidewall 22), approximately one-half inch high, and approximately one-half inch thick. It should be appreciated that the shape, size, topology, and placement of header block 14 relative to housing 12 may vary from one application to another, and that the particular configuration shown in FIG. 1 represents only one practical example. In this regard, header block 14 may, but need not, have a "tail" 26 that extends partially down sidewall 20. Alternate embodiments may include a longer or shorter tail 26, depending upon the desired locations of electrical connections and interface points, or depending upon the layout and routing of conductive elements contained within header block 14 and tail 26. In addition, header block 14 need not be located on upper sidewall 22 (or any sidewall) and may instead be located on one of the planar major sides of housing 12. Furthermore, more than one header block 12 may be utilized in a practical implementation.

Figure 2:
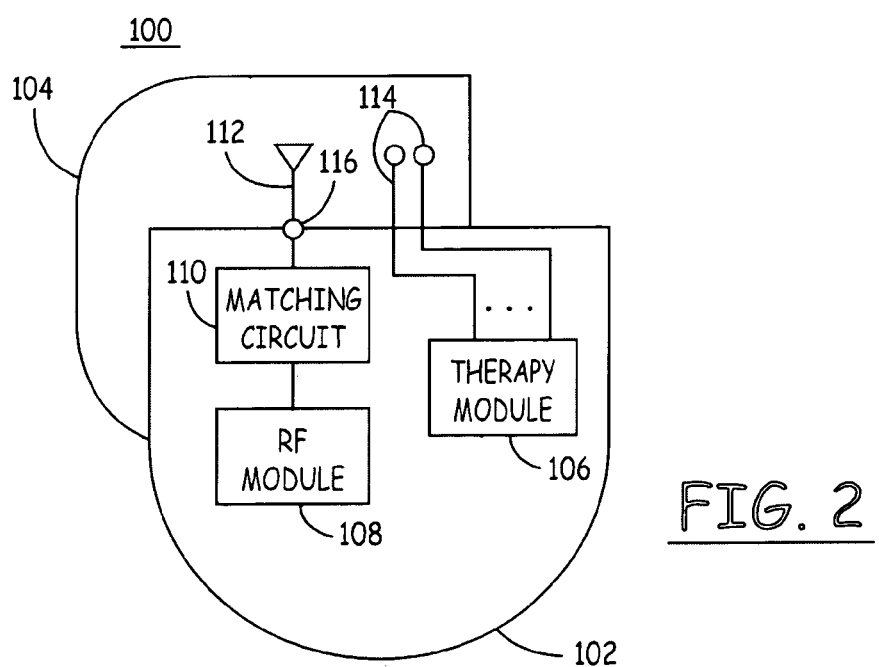
FIG. 2 is a schematic representation of an IMD and functional elements associated with the IMD.

FIG. 2 is a schematic representation of an IMD 100 and several functional elements associated therewith. IMD 100 generally includes a housing 102, a header block 104 coupled to housing 102, a therapy module 106 contained within housing 102, an RF module 108 contained within housing 102, an RF impedance matching circuit 110, which may also be contained within housing 102, and a telemetry antenna 112 that is suitably configured to facilitate far field data communication with an EMD. Housing 102 and header block 104 may be configured as described above in connection with FIG. 1. In practice, IMD 100 will also include a number of conventional components and features necessary to support the functionality of IMD 100. Such conventional elements will not be described herein.

Therapy module 106 may include any number of components, including, without limitation: electrical devices, ICs, microprocessors, controllers, memories, power supplies, and the like. Briefly, therapy module 106 is configured to provide the desired functionality associated with the IMD 100, e.g., defibrillation pulses, pacing stimulation, patient monitoring, or the like. In this regard, therapy module 106 may be coupled to one or more therapy lead connectors 114, which may be located within header block 104. In turn, therapy lead connectors 114 are electrically coupled to therapy leads (not shown) that extend from header block 104 for routing and placement within the patient.

RF module 108 may include any number of components, including, without limitation: electrical devices, ICs, amplifiers, signal generators, a receiver and a transmitter (or a transceiver), modulators, microprocessors, controllers, memories, power supplies, and the like. Although matching circuit 110 is illustrated as a separate component coupled to RF module 108, it may instead be incorporated into RF module 108 in a practical embodiment. Briefly, RF module 108 supports RF telemetry communication for IMD 100, including, without limitation: generating RF transmit energy; providing RF transmit signals to antenna 112; processing RF telemetry signals received by antenna 112, and the like. In practice, RF module 108 may be designed to leverage the conductive material used for housing 102 as an RF ground, and RF module 108 may be designed in accordance with the intended application of IMD 100, the electrical characteristics of the environment surrounding the implant location, the desired operating frequency range, the desired RF antenna range, and other practical considerations.

Matching circuit 110 may include any number of components, including, without limitation: electrical components such as capacitors, resistors, or inductors; filters; baluns; tuning elements; varactors; limiter diodes; or the like. Matching circuit 110 is suitably configured to provide impedance matching between antenna 112 and RF module 108, thus improving the efficiency of antenna 112. Matching circuit 110 may leverage known techniques to alter the electrical characteristics of antenna 112 to suit the needs of the particular application. For example, matching circuit 110 may be suitably configured to enhance the far field radiation characteristics of antenna 112 while allowing antenna 112 to be physically compact and conformal for practical deployment in an IMD 100 having relatively strict physical size limitations.

RF module 108 and/or matching circuit 110 may also be configured to support the particular design and intended operation of antenna 112. For example, antenna 112 may have characteristics resembling a monopole antenna, characteristics resembling a dipole antenna, characteristics resembling a balanced antenna, characteristics resembling an unbalanced antenna, characteristics resembling a coplanar waveguide antenna, characteristics resembling a stripline antenna, characteristics resembling a microstrip antenna, and/or characteristics resembling a transmission line antenna. Antenna 112 may also have any number of radiating elements, which may be driven by any number of distinct RF signal sources. In this regard, antenna 112 may have a plurality of radiating elements configured to provide spatial or polarization diversity. In view of the different practical options for antenna 112, RF module 108 and/or matching circuit 110 can be customized in an appropriate manner.

Antenna 112 is coupled to matching circuit 110 and/or to RF module 108 to facilitate RF telemetry between IMD 100 and an EMD (not shown). Generally, antenna 112 is suitably configured for UHF or VHF operation. Depending upon the specific embodiment of the invention, a portion of antenna 112 may be located within header block 104 and/or a portion of antenna 112 may be located within a dielectric sheath coupled to housing 102 (the dielectric sheath is not shown in FIG. 2). In practice, antenna 112 may be encapsulated by the dielectric material used to form header block 104 and/or by the dielectric material used to form the sheath. Antenna 112 (or at least a radiating element of antenna 112) is coupled to matching circuit 110 and/or to RF module 108 via at least one RF feedthrough 116, which bridges housing 102. Briefly, a practical RF feedthrough 116 includes a ferrule supporting a non-conductive glass or ceramic annular insulator. The insulator supports and electrically isolates a feedthrough pin from the ferrule. During assembly of housing 102, the ferrule is welded to a suitably sized hole or opening formed in housing 102. Matching circuit 110 and/or RF module 108 is then electrically connected to the inner end of the feedthrough pin. The connection to the inner end of the feedthrough pin can be made by welding the inner end to a substrate pad, or by clipping the inner end to a cable or flex wire connector that extends to a substrate pad or connector. The outer end of the feedthrough pin serves as a connection point for antenna 112.

In FIG. 2, RF feedthrough 116 is located on the upper perimeter sidewall of housing 102 such that it defines a feed point for antenna 112, leading from housing 102 into header block 104. Alternatively, RF feedthrough 116 may be located on the lower perimeter sidewall of housing 102, on either of the major perimeter sidewalls of housing 102, or on either of the major sides of housing 102. Consequently, any of the antenna arrangements described herein may be modified to accommodate different RF feedthrough locations. For example, a given antenna may utilize an input section that leads from the RF feedthrough location to the main section of the header block. Furthermore, depending upon the specific configuration and topology of antenna 112, a single RF feedthrough may provide insulated routing for any number of separate radiating elements, and/or IMD 100 may include any number of separate RF feedthroughs for a like number of separate antenna elements.

Figure 3:
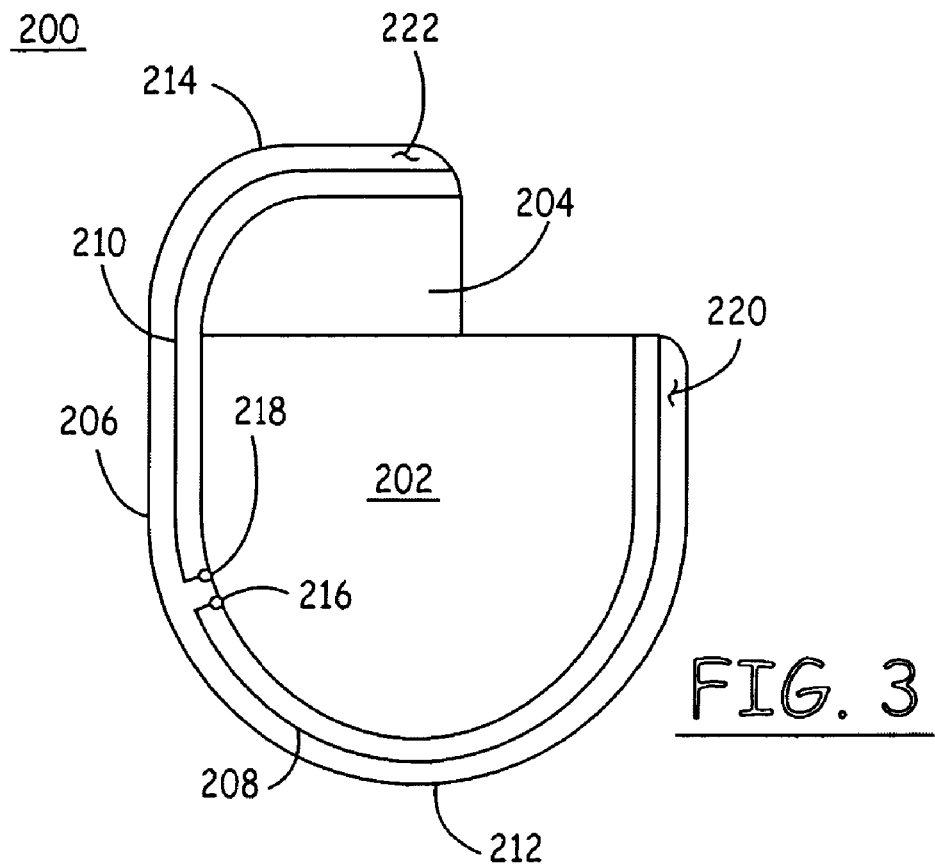
FIG. 3 is a front view of an IMD configured in accordance with one embodiment of the invention.
Figure 4:
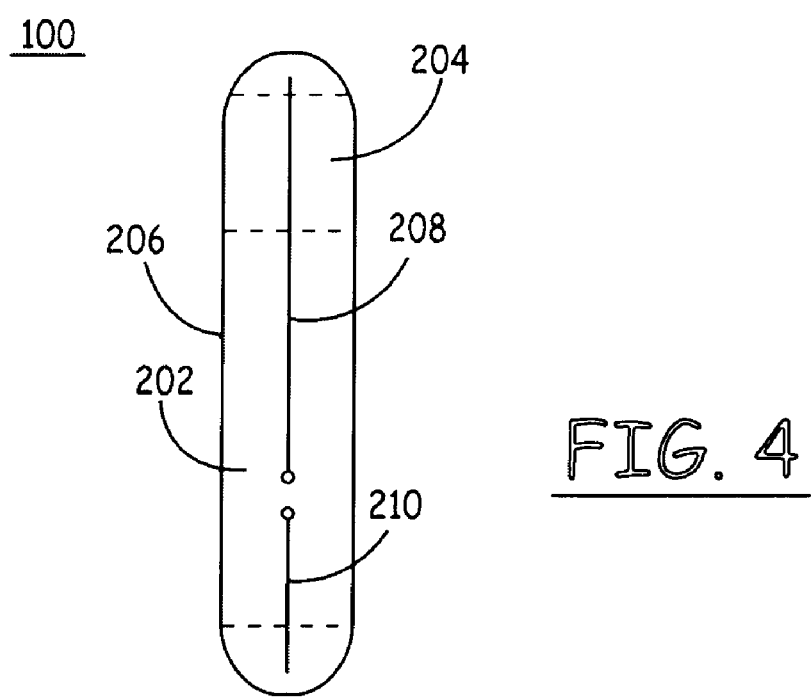
FIG. 4 is a side edge view of the IMD shown in FIG. 3.
Figure 5:
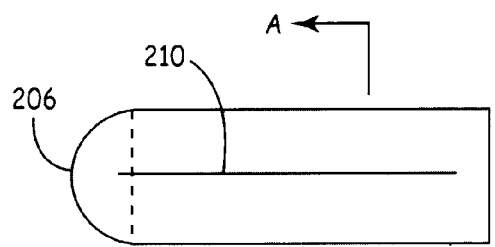
FIG. 5 is a top view of the header block portion of the IMD shown in FIG. 3.
Figure 6:
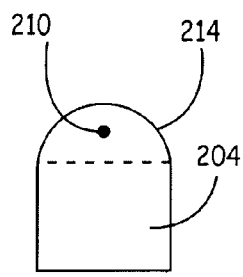
FIG. 6 is a cross sectional view of the header block portion of the IMD shown in FIG. 3, as viewed along line A-A in FIG. 5.

FIG. 3 is a front view of an IMD 200 configured in accordance with one example embodiment of the invention, FIG. 4 is a side edge view of IMD 200, FIG. 5 is a top view of the header block portion of IMD 200, and FIG. 6 is a cross sectional view of the header block portion as viewed along line A-A in FIG. 5. Certain features and aspects of IMD 200 are similar to those described above in connection with IMD 10 and IMD 100, and shared features and aspects will not be redundantly described in the context of IMD 200. IMD 200 generally includes a housing 202, a header block 204 coupled to housing 202, a dielectric sheath 206 coupled to housing 202 and/or to header block 204, and an antenna arrangement comprising a first antenna element 208 and a second antenna element 210.

Dielectric sheath 206 has a first section 212 that is located around at least a portion of the perimeter of housing 202, and a second section 214 that is located around at least a portion of the perimeter of header block 204. In this particular embodiment, first section 212 traverses the entire lower perimeter edge of housing 202, and second section 214 traverses the entire upper perimeter edge of header block 204. The actual configuration and length of dielectric sheath 206 may vary to suit the needs of the given IMD. For example, in some embodiments, second section 214 of dielectric sheath 206 may be integrated with header block 204. Dielectric sheath 206 is preferably formed from a suitable dielectric material, such as a biocompatible synthetic polymer, or any material suitable for use with header block 204. In some embodiments, the dielectric material of dielectric sheath 206 passes RF energy that is radiated or received by antenna elements 208/210 encapsulated within dielectric sheath 206. The encapsulation of antenna elements 208/210 within dielectric sheath 206 insulates the antenna arrangement from the tissue and fluids after implantation. The specific material for dielectric sheath 206 may be chosen in response to the intended application of IMD 200, the electrical characteristics of the environment surrounding the implant location, the desired operating frequency range, the desired RF antenna range, and other practical considerations.

In this particular embodiment, antenna elements 208/210 are completely contained within dielectric sheath 206. In practice, antenna elements 208/210 may be encapsulated within the dielectric material that forms dielectric sheath 206. In the example embodiment, antenna element 208 makes electrical contact with an RF feedthrough 216 and antenna element 210 makes electrical contact with an RF feedthrough 218 when dielectric sheath 206 is coupled to housing 202. In this regard, antenna elements 208/210 have respective feed points located on the perimeter of housing 202. In the example embodiment, the two feed points are adjacent and in close proximity to one another. In accordance with known techniques, antenna elements 208/210 may be attached to the respective feedthrough pins via welding, and a biocompatible medical adhesive or epoxy may be used to cover and electrically insulate any exposed portions of the feedthrough pins or antenna elements 208/210. It should be appreciated that, in a practical embodiment, RF feedthroughs 216/218 may be located anywhere along the perimeter of housing 202, and the specific location shown in FIG. 3 and FIG. 4 represents only one suitable example.

Antenna element 208 includes an endpoint 220 located in first section 212 of dielectric sheath 206, and antenna element 210 includes an endpoint 222 located in second section 214 of dielectric sheath 206. In this example embodiment, both endpoints 220/222 are floating endpoints (i.e., the ends of antenna elements 208/210 are left ungrounded). When configured with floating endpoints 220/220, the antenna arrangement forms a balanced antenna arrangement that need not rely on a ground plane structure for operation. In alternate embodiments of the invention, endpoint 220 and/or endpoint 222 may be grounded, thus forming an unbalanced antenna arrangement.

The antenna arrangement is preferably dimensioned and otherwise configured to fit within the space limitations of dielectric sheath 206. In addition, the antenna arrangement is dimensioned to provide far field radiation of RF transmit energy provided by the RF module contained within housing 202. For example, when antenna elements 208/210 form a balanced antenna arrangement, they are suitably configured to have an equal electrical length (which may not coincide with an equal physical length). In addition, the RF module is suitably configured to drive the antenna elements 180 degrees out of phase. Thus, in a practical balanced antenna embodiment, antenna elements 208/210 are separate and isolated radiating elements that are driven independently by the RF module, which may incorporate a balun circuit to convert an unbalanced RF signal into balanced RF signal feeds.

In accordance with one practical application, the antenna arrangement is suitably dimensioned and tuned for reception and transmission of RF signals having a carrier frequency within the range of 402 MHz to 405 MHz. The antenna arrangement is preferably dimensioned and tuned to account for the intended operating environment (IMD 200 is surrounded by conductive body tissue when deployed) and to account for the desired far field operating range. In this regard, the antenna arrangement is preferably designed to meet system requirements for a two-meter minimum telemetry range and to provide adequate gain, gain pattern, bandwidth, and tunability using one or more reactive elements for different possible environments before and after implanting of IMD 200.

As shown in FIG. 3, each antenna element 208/210 may be shaped such that its profile forms a simple curve (when viewed from the perspective of FIG. 3). The curved shape enables the antenna arrangement to assume a compact form within dielectric sheath 206 while maintaining the desired electrical length necessary for good far field telemetry performance. As depicted in FIG. 3, antenna element 208 is generally oriented in a first direction relative to dielectric sheath 206 (e.g., a counterclockwise direction around the perimeter of housing 202), while antenna element 210 is generally oriented in a second and opposing direction relative to dielectric sheath 206 (e.g., a clockwise direction around the perimeter of housing 202 and around the perimeter of header block 204). The respective origination sections of antenna elements 208/210 may be suitably bent (as shown in FIG. 3) or curved to accommodate the transition from housing 202 to the respective traversing paths within dielectric sheath 206. Antenna elements 208/210 may be curved such that they define a plane that is generally parallel to a major side or sides of housing 202 and/or generally parallel to a major side or sides of header block 204 (see FIG. 4). In the example embodiment, antenna elements 208/210 are evenly spaced between the two major sides of header block 204 and evenly spaced between the two major sides of housing 202, thus eliminating a potential source of asymmetry. In one practical embodiment, antenna elements 208/210 are located in header block 204 such that they are as far away from housing 202 as possible while still being insulated from body tissue.

To implement effective telemetry from a given IMD over the desired distances, the driving power should be efficiently converted to maximize the far field component generated by the antenna arrangement. One factor affecting the far field component is the length of antenna elements 208/210 with respect to the wavelength of the radiating RF carrier signal. While many types of antennas function according to a variety of parameters, it is generally desirable to provide an antenna element having a minimum length equivalent to one-quarter or one-half the wavelength of the RF carrier signal. Other factors include the dielectric values imposed by the surrounding medium, e.g., housing 202, header block 204, dielectric sheath 206, and the surrounding patient environment.

Figure 7:
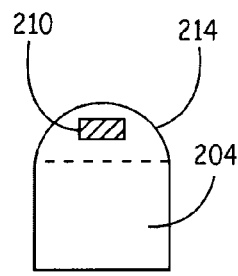
FIG. 7 is a cross sectional view of a header block portion of an IMD configured in accordance with an alternate embodiment of the invention.
Figure 8:
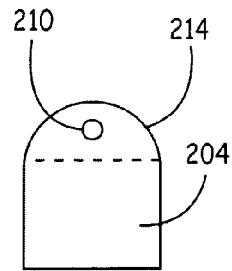
FIG. 8 is a cross sectional view of a header block portion of an IMD configured in accordance with another alternate embodiment of the invention.

Each antenna element 208/210 may include a radiating element formed from a conductive wire, such as a titanium wire, a niobium wire, or the like. As shown in the cross sectional view of FIG. 6, antenna elements 208/210 may be formed from a solid wire having a round cross section. In practical embodiments, antenna elements 208/210 may be formed from a round wire having a diameter of approximately 0.020 inches. Alternatively, as depicted in FIG. 7, antenna elements 208/210 may be formed from a flat wire, a flat ribbon element, or a stamped conductor having a generally rectangular cross section (or any practical cross sectional shape). FIG. 8 depicts yet another embodiment where antenna elements 208/210 are formed from a hollow wire having a round ring shaped cross section. FIG. 3 equivalently depicts any embodiment that employs antenna elements having relatively thin profiles or heights, and FIGS. 4 and 5 equivalently depict any embodiment that employs relatively thin conductors or wires for antenna elements 208/210.

Antenna elements 208/210 need not be limited to the shapes illustrated herein. Rather, antenna elements 208/210 (or portions thereof) may be coiled, may follow a curved, zig-zag, serpentine, square wave, or other path. Furthermore, antenna elements 208/210 (or portions thereof) may be realized as composite structures, e.g., a radiating element surrounded by dielectric material, a coaxial cable arrangement, or the like.

Figure 9:
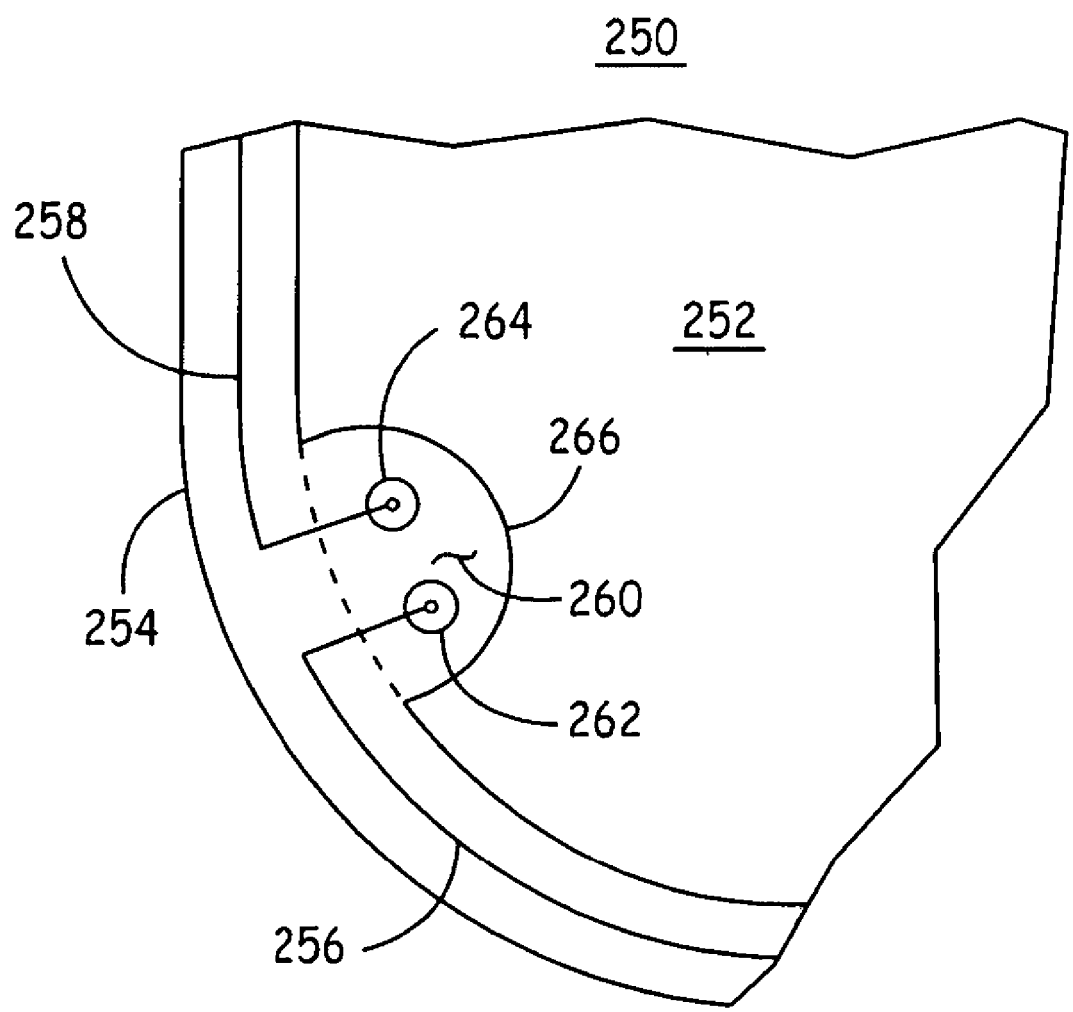
FIG. 9 is a front view of a detailed portion of an IMD configured in accordance with an alternate embodiment of the invention.

FIG. 9 is a front view of a detailed portion of an IMD 250 configured in accordance with an alternate embodiment of the invention. Certain features and aspects of IMD 250 are similar to those described above in connection with IMD 200, and shared features and aspects will not be redundantly described in the context of IMD 250. The detailed section shown in FIG. 9 includes a portion of a housing 252, a portion of a dielectric sheath 254, a portion of a first antenna element 256, and a portion of a second antenna element 258. In contrast to IMD 200, antenna elements 256/258 include respective feed points located on a major side of housing 252, e.g., the front face of housing 252. In this embodiment, the respective origination sections of antenna elements 256/258 may be offset or otherwise contoured to accommodate the transition from the face of housing 252 to the respective traversing paths within dielectric sheath 254. Housing 252 may include a depression or other feature 260 for positioning of the RF feedthroughs 262/264 for antenna elements 256/258. In addition, dielectric sheath 254 may include a suitably configured "bulge" or extension 266 that covers RF feedthroughs 262/264 and the origination sections of antenna elements 256/258. In a practical embodiment, RF feedthroughs 262/264, depression 260, and extension 266 may be located anywhere on housing 252, and the specific location shown in FIG. 9 represents only one suitable example.

FIGS. 10-19 are front views of different IMDs configured in accordance with alternate embodiments of the invention. Certain features and aspects of these IMDs may be similar to those described above in connection with IMD 10, IMD 100, IMD 200, and IMD 250, and shared features and aspects will not be redundantly described in the context of these alternate embodiments.

Figure 10:
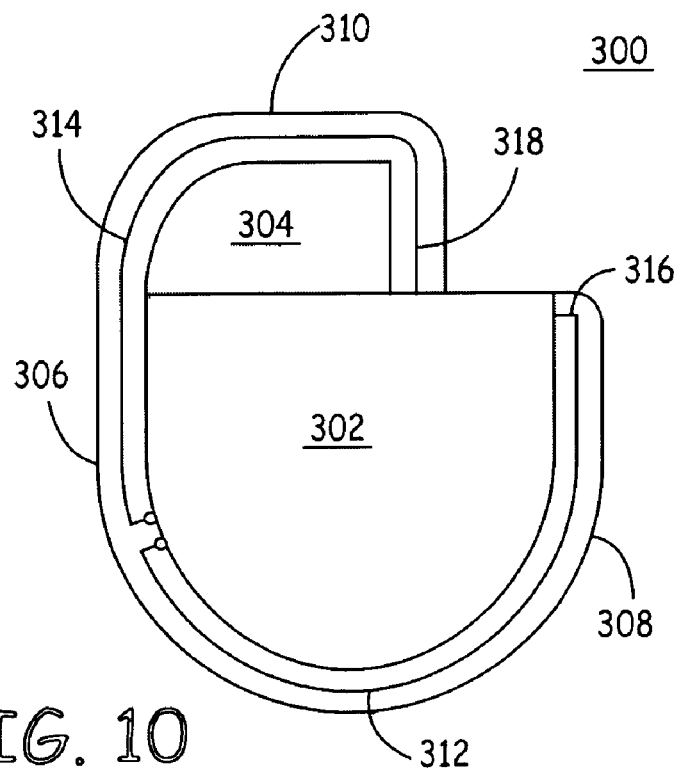
FIGS. 10-19 are front views of IMDs configured in accordance with alternate embodiments of the invention.

FIG. 10 shows an IMD 300 that is similar to IMD 200 (see FIG. 3). IMD 300 generally includes a housing 302, a header block 304 coupled to housing 302, a dielectric sheath 306 coupled to housing 302 and/or to header block 304, and a two-element antenna arrangement protected by dielectric sheath 306. Dielectric sheath 306 includes a first section 308 configured for positioning around at least a portion of the perimeter of housing 302, and a second section 310 configured for positioning around at least a portion of the perimeter of header block 304. In this embodiment, first section 308 spans the entire lower perimeter of housing 302, and second section 310 spans the entire perimeter of header block 304.

The antenna arrangement of IMD 300 includes a first antenna element 312 and a second antenna element 314. Each antenna element 312/314 has a feed point originating from housing 302. In contrast to IMD 200, however, each antenna element 312/314 has a grounded endpoint. In this example, antenna element 312 has a grounded endpoint 316 at a major sidewall of housing 302, and antenna element 314 has a grounded endpoint 318 at the upper sidewall of housing 302. Grounded endpoints 316/318 may be connected to a conductive portion of housing 302, or they may be connected to RF feedthroughs (not shown in FIG. 10) for coupling to an RF ground potential on the RF module contained within housing 302. The grounding of endpoints 316/318 creates an unbalanced antenna arrangement that depends upon the RF ground potential for operation.

Figure 11:
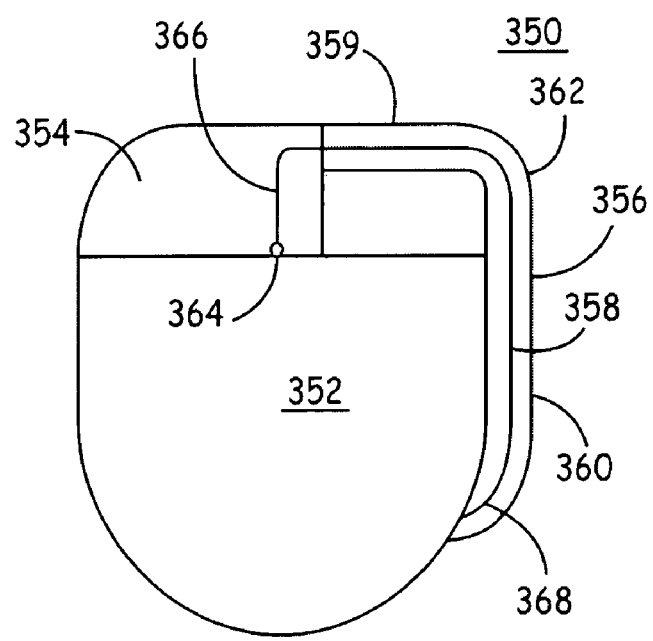

FIG. 11 shows an IMD 350 that generally includes a housing 352, a header block 354 coupled to housing 352, a dielectric sheath 356 coupled to housing 352 and/or to header block 354, and an antenna element 358 contained within dielectric sheath 356. Dielectric sheath 356 includes a first section 359 that extends from header block 354 in a generally straight direction, and a second section 360 located around at least a portion of the perimeter of housing 352. In practice, second section 360 may be of any desired length, and second section 360 may extend further around the perimeter of housing 352 to header block 354. In this example embodiment, first section 359 and second section 360 are coupled together via a bend section 362, and dielectric sheath 356 forms an "air bridge" over a portion of the upper edge of housing 352.

Antenna element 358 has a feed point 364 located within header block 354 such that antenna element 358 originates from a section of housing 352 covered by header block 354. Consequently, an origination section 366 of antenna element 358 may be contained within header block 354. In the illustrated embodiment, origination section 366 travels upward through header block 354 until it reaches a level that is approximately aligned with first section 359 of dielectric sheath 356. At this level, origination section 366 bends to accommodate the transition from header block 354 to first section 359 of dielectric sheath 356. In accordance with one practical embodiment of IMD 350, origination section 366 of antenna element 358 is a coaxial antenna section, while the remaining section of antenna element 358 represents the conductive wire of the coaxial antenna section (where the other components of the coaxial antenna have been stripped away). The remaining section of antenna element 358 is contained within dielectric sheath 356 as shown in FIG. 11. In the illustrated embodiment, antenna element 358 includes a floating endpoint 368. Alternatively, endpoint 368 may be grounded as described above in connection with IMD 300.

Figure 12:
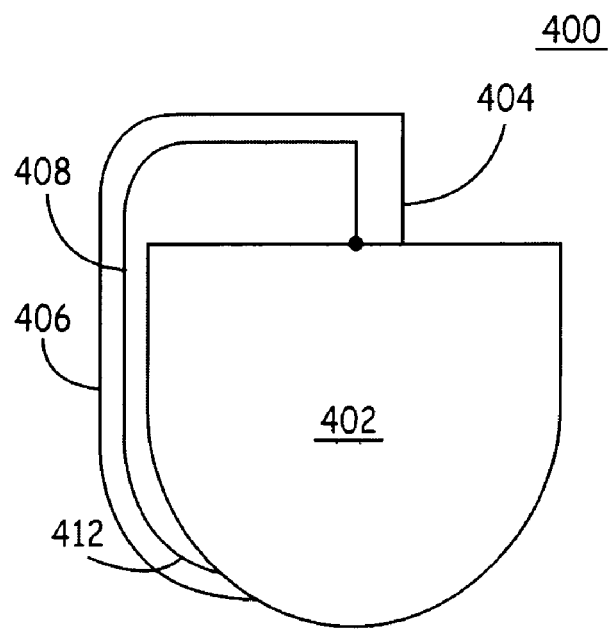

FIG. 12 shows an IMD 400 that generally includes a housing 402, a header block 404 coupled to housing 402, a dielectric sheath 406 coupled to housing 402 and/or to header block 404, and an antenna element 408. IMD 400 is similar to IMD 300, however, header block 404 is integrated with dielectric sheath 406, and IMD 400 does not include an air bridge formed by dielectric sheath 406. Antenna element 408 has a feed point 410 located within header block 404 such that antenna element 408 originates from a section of housing 402 covered by header block 404. In the illustrated embodiment, antenna element 408 travels upward through header block 404, bends or curves toward one side of housing 402, then bends or curves downward into dielectric sheath 406. In the illustrated embodiment, antenna element 408 includes a floating endpoint 412. Alternatively, endpoint 412 may be grounded as described above in connection with IMD 300.

Figure 13:
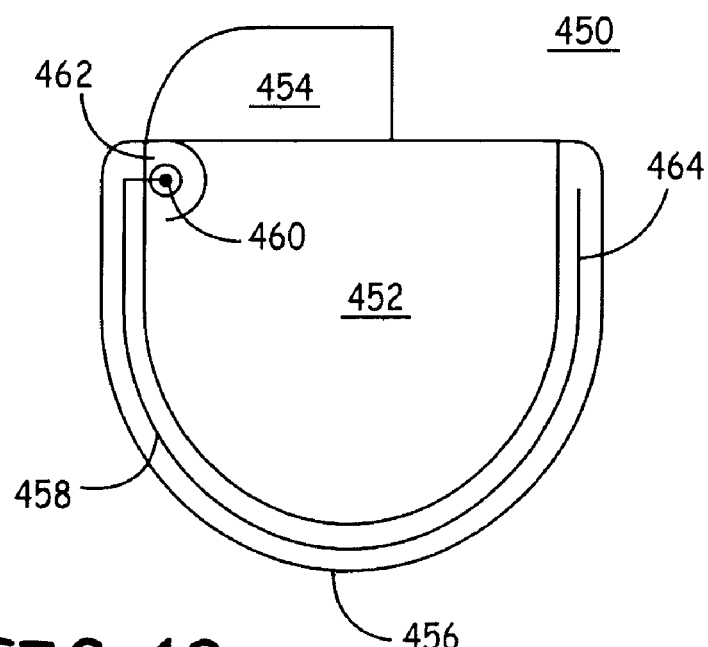

FIG. 13 shows an IMD 450 that generally includes a housing 452, a header block 454 coupled to housing 452, a dielectric sheath 456 coupled to housing 452, and an antenna element 458 contained within dielectric sheath 456. In practice, dielectric sheath 456 may be of any desired length to accommodate the desired length of antenna element 458. In this example, antenna element 458 has a feed point 460 on the front face of housing 452. As described above in connection with IMD 250, antenna element 458 may be bent or contoured to accommodate the transition from feed point 460 to the outer perimeter of housing 452. As described above in connection with IMD 250, dielectric sheath 456 may include an extension 462 that covers feed point 460 and a portion of the front face of housing 452. In practice, most of antenna element 458 resides within dielectric sheath 456, as shown in FIG. 13. In the illustrated embodiment, antenna element 458 is routed from feed point 460 to the perimeter of housing 452, then travels around the perimeter of housing 452 within dielectric sheath 456. In the illustrated embodiment, antenna element 458 includes a floating endpoint 464. Alternatively, endpoint 464 may be grounded as described above in connection with IMD 300.

Figure 14:
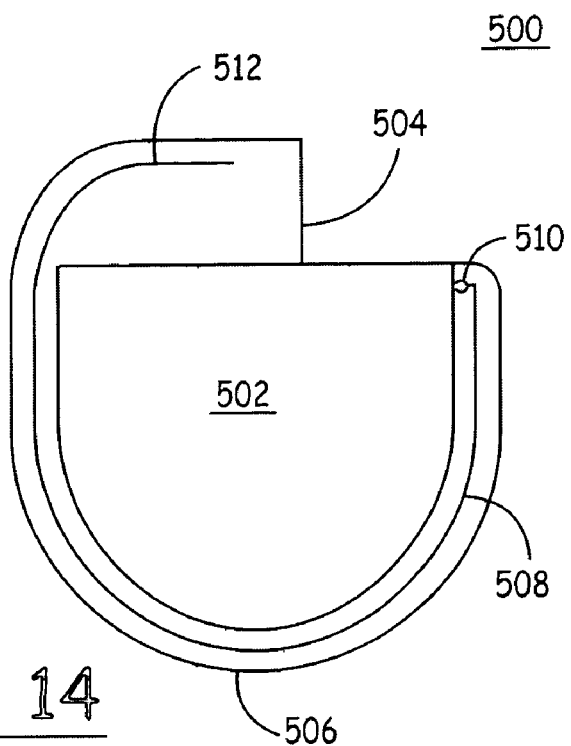

FIG. 14 shows an IMD 500 that generally includes a housing 502, a header block 504 coupled to housing 502, a dielectric sheath 506 coupled to housing 502 and/or to header block 504, and an antenna element 508 contained within dielectric sheath 506 and/or within header block 504. In this embodiment, dielectric sheath 506 is integrated with header block 504. In an alternate embodiment, dielectric sheath 506 may be a distinct component that is located above at least a portion of header block 504, as described above in connection with IMD 200. In practice, dielectric sheath 506 may be of any desired length to accommodate the desired feed point and length of antenna element 508. In this example, antenna element 508 has a feed point 510 on a perimeter sidewall of housing 502, and feed point 510 is contained within dielectric sheath 506. In the illustrated embodiment, antenna element 508 is routed from feed point 510, within dielectric sheath 506, and into header block 504. In this example, antenna element 508 includes a floating endpoint 512. Alternatively, endpoint 512 may be grounded as described above in connection with IMD 300.

Figure 15:
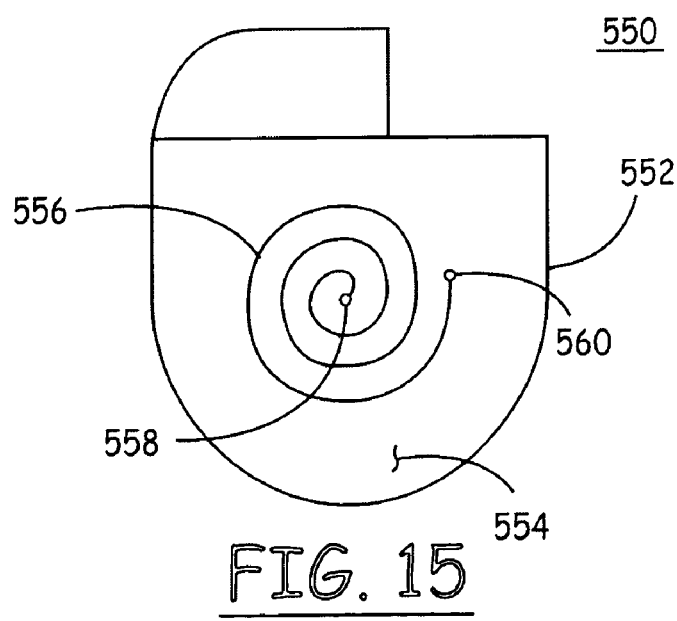

FIG. 15 shows an IMD 550 that generally includes a housing 552 having a major side 554 (e.g., the front side of IMD 550), and an antenna element 556 located on the exterior surface of major side 554. In this embodiment, antenna element 556 has a feed point 558 from major side 554 and a grounded endpoint 560. Endpoint 560 may be connected to housing 552 (assuming housing 552 serves as a conductive ground element) or to an RF feedthrough for connection to an RF ground potential located within housing 552. As depicted in FIG. 15, antenna element 556 is configured to form a two-dimensional inductive coil radiator on the exterior surface of major side 554. The number of coils, the length of antenna element 556, the curvature and tightness of the coils, the separation distance between coil windings, the overall size of antenna element 556, and other topology features of antenna element 556 will be dictated by the desired performance characteristics.

In practice, antenna element 556 will follow the contour of the exterior surface of major side 554. If housing 552 is formed from a conductive material, then IMD 550 may include a dielectric coating or layer between housing 552 and antenna element 556. In addition, IMD 550 may include a dielectric coating or radome (not shown) formed over antenna element 556. The dielectric coating insulates antenna element 556 from the tissue and fluids after implantation, and the material used for the dielectric coating may be chosen in response to the intended application of IMD 550, the electrical characteristics of the environment surrounding the implant location, the desired operating frequency range, the desired RF antenna range, and other practical considerations.

In an alternate embodiment of IMD 550, a similar antenna element is located on the opposing major side of housing 552, e.g., the rear face of IMD 550, which is hidden from view in FIG. 15. A dual antenna embodiment may be desirable to provide spatial diversity and/or polarization diversity for IMD 550.

Figure 16:
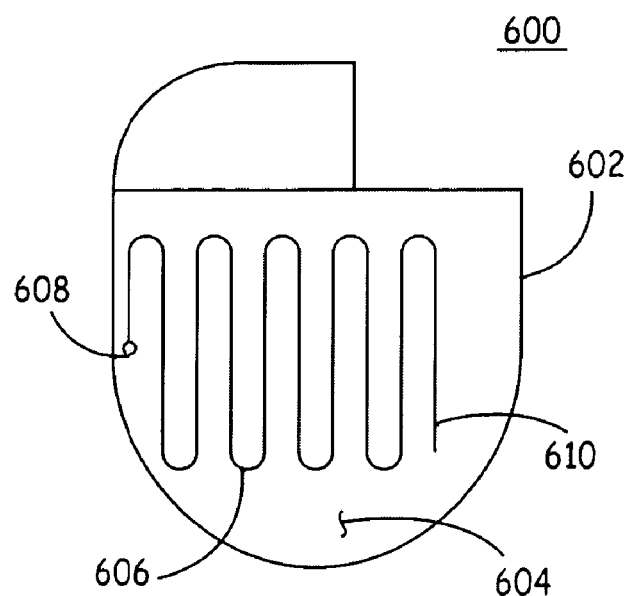

FIG. 16 shows an IMD 600 that generally includes a housing 602 having a major side 604 (e.g., the front side of IMD 600), and an antenna element 606 located on the exterior surface of major side 604. In this embodiment, antenna element 606 has a feed point 608 from major side 604, and a floating endpoint 610. Alternatively, endpoint 610 may be a grounded endpoint that is connected to a conductive portion of housing 602, or connected to an RF feedthrough (not shown in FIG. 16) for coupling to an RF ground potential on the RF module contained within housing 602. As depicted in FIG. 16, antenna element 606 has a serpentine or "meandering line" shape between feed point 608 and endpoint 610, which allows IMD 600 to incorporate a long antenna in a compact space. The number of turns in antenna element 606, the length of antenna element 606, the curvature of antenna element 606, the overall size of antenna element 606, and other topology features of antenna element 606 will be dictated by the desired performance characteristics.

IMD 600 may share several of the features of IMD 550, and such shared features will not be redundantly described in detail. For example, antenna element 606 may follow the contour of the exterior surface of major side 604, IMD 600 may include a dielectric coating or layer between housing 602 and antenna element 606, and IMD 600 may include a dielectric coating or radome formed over antenna element 606. Furthermore, an alternate embodiment of IMD 600 may include a similar antenna element located on the opposing major side of housing 602 to provide spatial diversity and/or polarization diversity for IMD 600.

Figure 17:
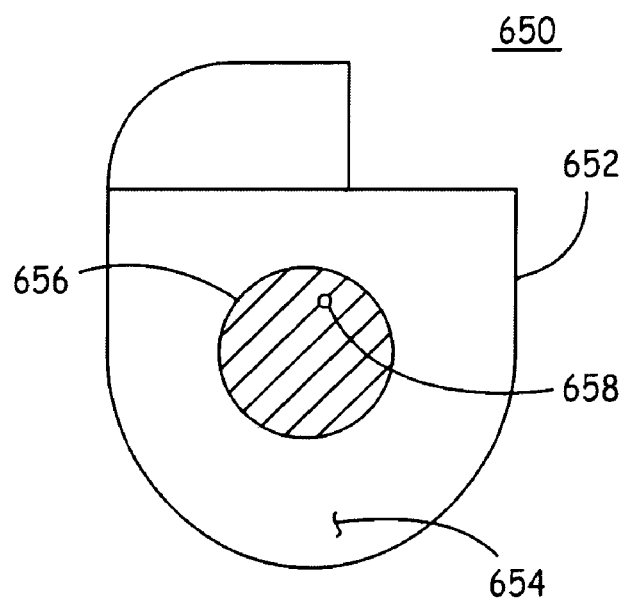

FIG. 17 shows an IMD 650 that generally includes a housing 652 having a major side 654 (e.g., the front side of IMD 650), and an antenna element 656 located on the exterior surface of major side 654. In this embodiment, antenna element 656 has a feed point 658 from major side 654, where feed point 658 may correspond to a conductive element of an RF feedthrough. As depicted in FIG. 17, antenna element 656 is suitably configured as a conductive patch or sheet coupled to the exterior surface of major side 654. The location of feed point 658 relative to antenna element 656 may vary depending upon the tuning of antenna element 656. In the example embodiment, antenna element 656 is circular in shape. The specific shape of antenna element 656, however, may be, without limitation: square, rectangular, oval, elliptical, or the like. Indeed, the size, shape, and other topology features of antenna element 656 will be dictated by the desired performance characteristics.

IMD 650 may share several of the features of IMD 550, and such shared features will not be redundantly described in detail. For example, antenna element 656 may follow the contour of the exterior surface of major side 654, IMD 650 may include a dielectric coating or layer between housing 652 and antenna element 656, and IMD 650 may include a dielectric coating or radome formed over antenna element 656. Furthermore, an alternate embodiment of IMD 650 may include a similar antenna element located on the opposing major side of housing 652 to provide spatial diversity and/or polarization diversity for IMD 650.

An IMD having a microstrip patch antenna is disclosed in U.S. Pat. No. 5,861,019, the content of which is incorporated by reference herein. It should be appreciated that IMD 650 may leverage certain features or aspects of the IMD antenna technology disclosed in this patent.

Figure 18:
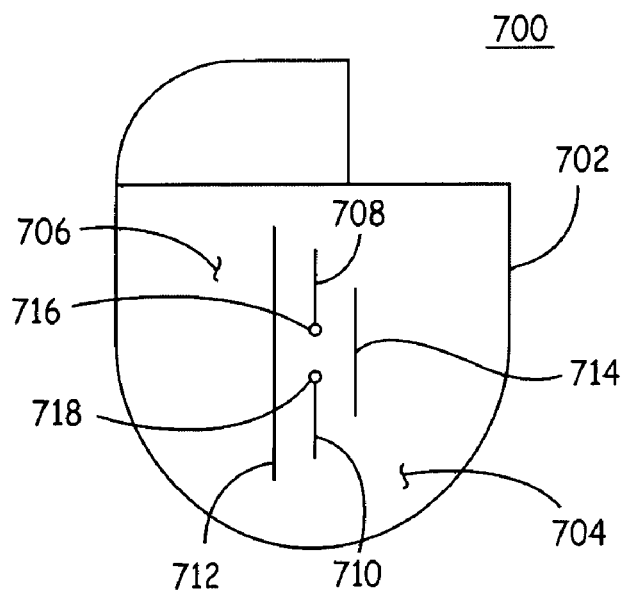

FIG. 18 shows an IMD 700 that generally includes a housing 702 having a major side 704 (e.g., the front side of IMD 700), and an antenna arrangement 706 located on the exterior surface of major side 704. Antenna arrangement 706 is configured as a surface mount Yagi-Uda antenna. The design and operation of such antennas are known to those skilled in the art and, therefore, will not be described in detail herein. Generally, antenna arrangement 706 includes at least one radiating element (IMD 700 includes two radiating or drive elements 708/710), a reflector element 712, and a director element 714, where all of these elements are formed from a conductive material such as a wire or a thin ribbon conductor. In the example embodiment, drive element 708 has a feed point 716 from major side 704, and drive element 710 has a feed point 718 from major side 704. Feed points 716/718 may be connected to (or correspond to) RF feedthroughs. The specific configuration of antenna arrangement 706, including the number of drive, reflector, and director elements, the shape and size of such elements, and other topology features of antenna arrangement 706 will be dictated by the desired performance characteristics.

IMD 700 may share several of the features of IMD 550, and such shared features will not be redundantly described in detail. For example, antenna arrangement 706 may follow the contour of the exterior surface of major side 704, IMD 700 may include a dielectric coating or layer between housing 702 and the antenna arrangement 706, and IMD 700 may include a dielectric coating or radome formed over antenna arrangement 706. Furthermore, an alternate embodiment of IMD 700 may include a similar antenna arrangement located on the opposing major side of housing 702 to provide spatial diversity and/or polarization diversity for IMD 700.

Figures 19, 20:
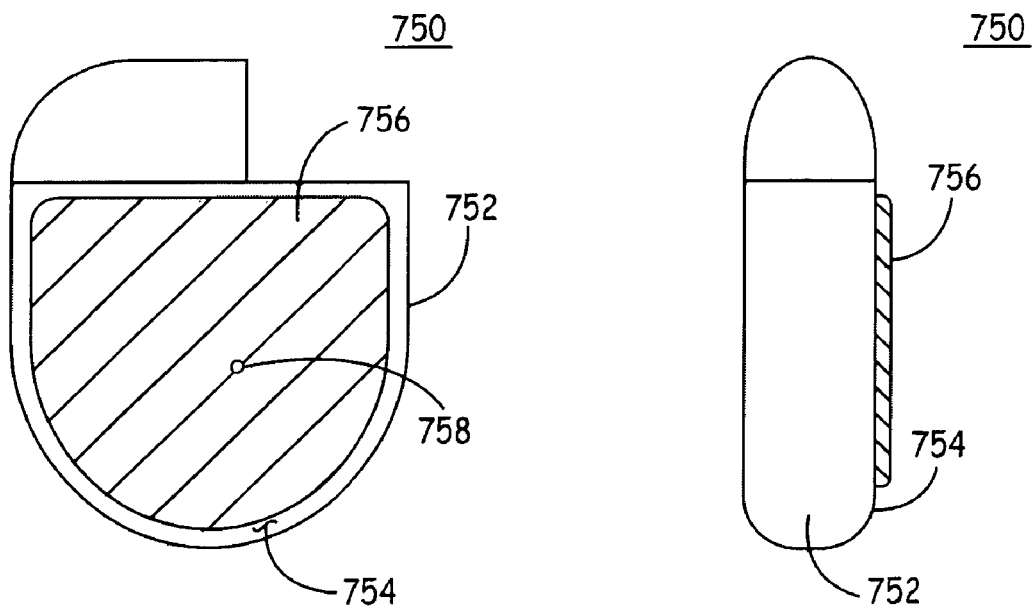
FIG. 20 is a side edge view of the IMD shown in FIG. 19.

FIG. 19 is a front view of an IMD 750, and FIG. 20 is a side edge view of IMD 750. IMD 750 generally includes a housing 752 having a major side 754 (e.g., the front side of IMD 750), and an antenna element 756 located on the exterior surface of major side 754. In this embodiment, antenna element 756 has a feed point 758 from major side 754, where feed point 758 may correspond to a conductive element of an RF feedthrough. Antenna element 756 is realized as a dielectric puck that serves as a resonator antenna. In this regard, antenna element 756 resonates at a certain frequency when excited by a suitable input signal via feed point 758. In practice, the dielectric material that forms antenna element 756 may be directly deposited onto housing 752. In accordance with one practical embodiment, antenna element 756 is formed from a high dielectric ceramic.

The location of feed point 758 relative to antenna element 756 may vary depending upon the tuning of antenna element 756. It should be appreciated that the specific shape of antenna element 756 may be square, rectangular, oval, elliptical, or the like, depending upon the desired resonant frequency. Indeed, the size, shape, and other topology features of antenna element 756 will be dictated by the desired performance characteristics.

IMD 750 may share several of the features of IMD 550, and such shared features will not be redundantly described in detail. For example, antenna element 756 may follow the contour of the exterior surface of major side 754, IMD 750 may include a dielectric coating or radome formed over antenna element 756, and an alternate embodiment of IMD 750 may include a similar antenna element located on the opposing major side of housing 752 to provide spatial diversity and/or polarization diversity for IMD 750.

Figure 21:
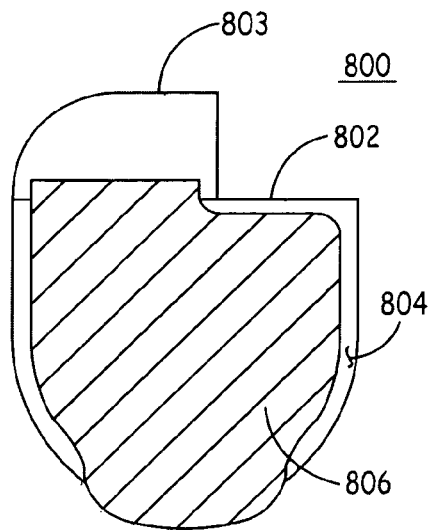
FIG. 21 is a front view of an IMD configured in accordance with an alternate embodiment of the invention.
Figure 22:
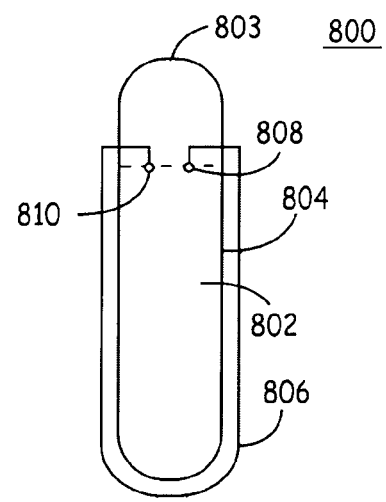
FIG. 22 is a side edge view of the IMD shown in FIG. 21.

FIG. 21 is a front view of an IMD 800, and FIG. 22 is a side edge view of IMD 800. IMD 800 generally includes a housing 802 having a major side 804 (e.g., the front side of IMD 800), a header block 803 coupled to housing 802, and a generally flat antenna element 806 that wraps around at least a portion of housing 802. In this embodiment, antenna element 806 has a feed point or section 808 located within header block 803; feed section 808 may originate at the upper perimeter edge of housing 802. Antenna element 806 also has a grounded endpoint or section 810 located within header block 803; grounded section 810 may be terminated at the upper perimeter edge of housing 802. In an alternate embodiment, endpoint/section 810 may remain ungrounded and floating within header block 803. In practice, antenna element 806 may be suitably configured as a conductive patch or sheet coupled to the exterior surface of housing 802, and the specific size, shape, and other topology features of antenna element 806 will be dictated by the desired performance characteristics.

IMD 800 may share several of the features of IMD 550, and such shared features will not be redundantly described in detail. For example, antenna element 806 may follow the contour of the exterior surface housing 802, IMD 800 may include a dielectric coating or layer between housing 802 and antenna element 806, and IMD 800 may include a dielectric coating or radome formed over antenna element 806.

A dipole version of IMD 800 (not shown) includes two separately driven antenna elements, each wrapping around at least a portion of housing 802 in opposite directions. For example, one antenna element may be a conductive sheet having a feed section at the bottom perimeter edge of housing 802 and an endpoint/section in header block 803, where the sheet wraps around the left side of IMD 800 (as viewed from the perspective of FIG. 22). A second antenna element may be a mirror image of the first antenna element, i.e., the second antenna element may be a conductive sheet having a separate feed section at the bottom perimeter edge of housing 802 and an endpoint/section in header block 803, where the second conductive sheet wraps around the right side of IMD 800.

Figure 23:
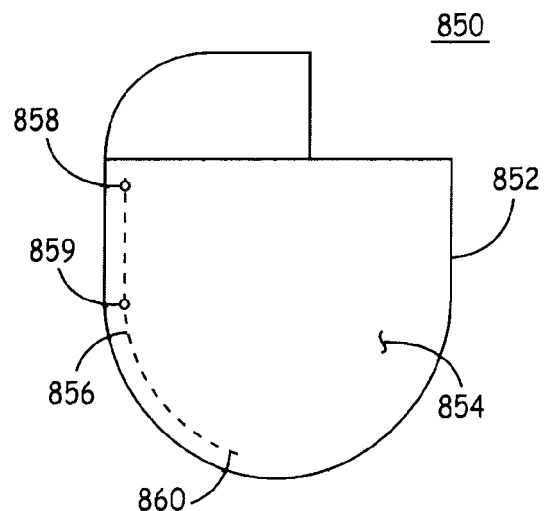
FIG. 23 is a front view of an IMD configured in accordance with an alternate embodiment of the invention.
Figure 24:
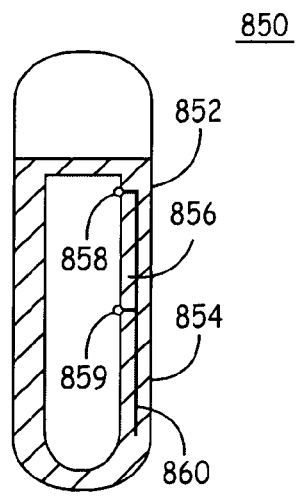
FIG. 24 is a side edge view of the IMD shown in FIG. 23.

FIG. 23 is a front view of an IMD 850, and FIG. 24 is a phantom side edge view of IMD 850 showing its internal configuration. IMD 850 generally includes a housing 852 having a major side 854 (e.g., the front side of IMD 850) and an antenna element 856. In this embodiment, antenna element 856 is embedded or encapsulated within a portion of housing 852 (e.g., major side 854), which is formed from a dielectric material such as alumina, titanium dioxide ceramic, or other ceramic material. The embedded nature of antenna element 856 is graphically depicted in FIG. 24, where the wall thickness of housing 852 has been exaggerated. In this embodiment, antenna element 856 has feed points 858/859 at the inner surface of major side 854 and antenna element 856 includes a bend or curve to accommodate the transition from feed points 858/859 into the dielectric portion of major side 854. Antenna element also has a floating endpoint 860 located within the dielectric portion of major side 854. Alternatively, endpoint 860 may be grounded via an RF feedthrough or via a connection to a conductive portion of housing 852. The length of antenna element 856, the curvature of antenna element 856, and other topology features of antenna element 856 will be dictated by the desired performance characteristics.

Depending upon the desired RF characteristics for the particular application, IMD 850 may include more than one antenna element (for example, in a dipole arrangement), any number of feed points, and different feed point locations than that depicted in FIG. 23 and FIG. 24. For example, two separate antenna conductors may be utilized, each having a distinct feed point (or feed points). In addition, the location of the feed point(s) may vary depending upon whether IMD 850 employs a ground plane. These and other practical variations may be implemented in an IMD having a housing that is formed at least in part by a dielectric material as described in the preceding paragraph.

FIG. 25 is a front view of an IMD 900, and FIG. 26 is a cross sectional view of IMD 900 as viewed along line B-B. IMD 900 generally includes a housing 902 having a major side 904 (e.g., the front side of IMD 900) and an antenna element 906. In this embodiment, antenna element 906 is configured as a sheet or plated element coupled to the interior side of major side 904, and at least major side 904 of housing 902 is formed from a dielectric material such as ceramic. The interior side of antenna element 906 may have a feed point (not shown) for the RF drive signal. In this regard, IMD 900 need not utilize an RF feedthrough because antenna element 906 and the RF module are both located within housing 902.

Antenna element 906 may be realized as a conductive patch or element that is plated or otherwise deposited directly onto dielectric major side 904. The location of the feed point relative to antenna element 906 may vary depending upon the tuning of antenna element 906. In the example embodiment, antenna element 906 is rectangular in shape. The specific shape of antenna element 906, however, may be, without limitation: square, circular, oval, elliptical, or the like. Indeed, the size, shape, and other topology features of antenna element 906 will be dictated by the desired performance characteristics.

IMD 900 may share several of the features of IMD 550, and such shared features will not be redundantly described in detail. For example, antenna element 900 may follow the contour of the interior surface of major side 904, IMD 900 may include a dielectric coating or radome formed over antenna element 906, and an alternate embodiment of IMD 900 may include a similar antenna element located on the opposing major side of housing 902 to provide spatial diversity and/or polarization diversity for IMD 900.

FIG. 27 shows an IMD 950 that generally includes a housing 952 having a major side 954 (e.g., the front side of IMD 950), and an antenna arrangement 956 coupled to major side 954. In this embodiment, antenna arrangement 956 comprises a radiating slot 958 formed within major side 954, a dielectric filler 960 deposited within radiating slot 958, and a feedpoint element 962 located within housing 952. In accordance with a practical embodiment of IMD 950, dielectric filler 960 is a material (such as ceramic) that is RF transparent or virtually RF transparent. Feedpoint element 962 includes one or connection points (not shown) for the RF drive signal. In this regard, IMD 950 need not utilize an RF feedthrough because feedpoint element 962 and the RF module are both located within housing 952. The design and operation of such slotted antennas are known to those skilled in the art and, therefore, will not be described in detail herein.

Feedpoint element 962 is formed from a conductive material such as a wire or a thin ribbon conductor. In the example embodiment, feedpoint element 962 is perpendicular to radiating slot 958, as shown in FIG. 27. IMD 950 may include a dielectric coating or layer between housing 952 and feedpoint element 962 to provide insulation. In addition, IMD 950 may include a dielectric coating, layer, or seal 964 formed over the interior components of antenna arrangement 956 (see FIG. 28). The specific configuration of antenna arrangement 956, including the shape and size of feedpoint element 962, the shape and size of radiating slot 958, the dielectric material utilized as dielectric filler 960, and other topology features of antenna arrangement 956 will be dictated by the desired performance characteristics. Furthermore, an alternate embodiment of IMD 950 may include a similar antenna arrangement located on the opposing major side of housing 952 to provide spatial diversity and/or polarization diversity for IMD 950.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

What is claimed is:

1. An implantable medical device ("IMD") comprising:
   a housing having a housing perimeter;
   a header block coupled to said housing, said header block having a header block perimeter;
   a dielectric sheath having a first section located around at least a portion of said housing perimeter, and a second section located around at least a portion of said header block perimeter, said dielectric sheath being a distinct component from said header block; and an antenna arrangement comprising a first antenna element completely contained within said dielectric sheath and having no portion located within said header block, and a second antenna element completely contained within said dielectric sheath and having no portion located within said header block, said second antenna element being physically distinct from said first antenna element;

said first antenna element having a first feed point from said housing and a first endpoint in said first section of said dielectric sheath;

said second antenna element having a second feed point from said housing and a second endpoint in said second section of said dielectric sheath, said second feed point being physically distinct from said first feed point; and said first feed point being adjacent to said second feed point.

2. An IMD according to claim 1, said first feed point and said second feed point being located on said housing perimeter.

3. An IMD according to claim 1, said first feed point and said second feed point being located on a major side of said housing.

4. An IMD according to claim 1, said first endpoint being a floating endpoint.

5. An IMD according to claim 4, said second endpoint being a floating endpoint, and said antenna arrangement being a balanced antenna arrangement.

6. An IMD according to claim 1, said first antenna element and said second antenna element having an equal electrical length.

7. An IMD according to claim 1, said first antenna element being oriented in a first direction relative to said dielectric sheath, and said second antenna element being oriented in a second direction relative to said dielectric sheath, said second direction opposing said first direction.

8. An implantable medical device ("IMD") comprising:
a housing having a housing perimeter;
a header block coupled to said housing, said header block having a header block perimeter;
a dielectric sheath having a first section located around at least a portion of said housing perimeter, and a second section located around at least a portion of said header block perimeter, said dielectric sheath being a distinct component from said header block;
an antenna arrangement comprising a first antenna element completely contained within said dielectric sheath and having no portion located within said header block, and a second antenna element completely contained within said dielectric sheath and having no portion located within said header block, said second antenna element being physically distinct from said first antenna element; and
a radio frequency ("RF") module contained in said housing and coupled to said antenna arrangement, said antenna arrangement being dimensioned to provide far field radiation of RF transmit energy provided by said RF module;

said first antenna element having a first feed point from said housing and a first endpoint in said first section of said dielectric sheath; and said second antenna element having a second feed point from said housing and a second endpoint in said second section of said dielectric sheath, said second feed point being physically distinct from said first feed point.

9. An IMD according to claim 8, said RF module being configured to drive said first antenna element and said second antenna element 180 degrees out of phase.

10. An IMD according to claim 8, said RF module being configured to drive said first antenna element and said second antenna element 90 degrees out of phase.

11. A far field telemetry antenna assembly for an implantable medical device ("IMD") having a housing and a header block, the housing having a housing perimeter and the header block having a header block perimeter, said antenna assembly comprising:
a dielectric sheath having a first section configured for positioning around at least a portion of the housing perimeter, and a second section configured for positioning around at least a portion of the header block perimeter, said dielectric sheath being a distinct component from said header block;
a first antenna element completely contained within said dielectric sheath without any portion thereof contained within said header block, and having a first feed point and a first endpoint, said first endpoint being located in said first section of said dielectric sheath; and
a second antenna element completely contained within said dielectric sheath without any portion thereof contained within said header block, and having a second feed point and a second endpoint, said second endpoint being located in said second section of said dielectric sheath, wherein said first antenna element and said second antenna element are physically distinct, and wherein said first feed point and said second feed point are physically distinct;
said first feed point being adjacent to said second feed point.

12. An antenna assembly according to claim 11, said dielectric sheath being formed from a dielectric material, and said first antenna element and said second antenna element being encapsulated by said dielectric material.

13. An antenna assembly according to claim 11, said first endpoint being a floating endpoint.

14. An antenna assembly according to claim 13, said second endpoint being a floating endpoint, and said first antenna element and said second antenna element forming a balanced antenna arrangement.

15. An antenna assembly according to claim 11, said first antenna element and said second antenna element having an equal electrical length.

16. An antenna assembly according to claim 11, said first antenna element being oriented in a first direction relative to said dielectric sheath, and said second antenna element being oriented in a second direction relative to said dielectric sheath, said second direction opposing said first direction.

* * * * *